United States Patent
Koch et al.

(10) Patent No.: US 9,944,614 B2
(45) Date of Patent: Apr. 17, 2018

(54) PRODUCTION OF FURFURAL FROM XYLOSE

(71) Applicant: BASF SE, Ludwigshafen (DE)

(72) Inventors: Stefan Koch, Mainz (DE); Alois Kindler, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/103,336

(22) PCT Filed: Dec. 10, 2014

(86) PCT No.: PCT/IB2014/066752
§ 371 (c)(1),
(2) Date: Jun. 10, 2016

(87) PCT Pub. No.: WO2015/087248
PCT Pub. Date: Jun. 18, 2015

(65) Prior Publication Data
US 2016/0304481 A1    Oct. 20, 2016

(30) Foreign Application Priority Data
Dec. 13, 2013  (EP) .................................... 13197237

(51) Int. Cl.
C07D 307/50  (2006.01)
(52) U.S. Cl.
CPC .................. C07D 307/50 (2013.01)
(58) Field of Classification Search
CPC .................................................. C07D 307/50
USPC ........................................................ 549/489
See application file for complete search history.

(56) References Cited

U.S. PATENT DOCUMENTS

| | | |
|---|---|---|
| 4,533,743 A | 8/1985 | Medeiros et al. |
| 7,572,925 B2 | 8/2009 | Dumesic et al. |
| 8,524,924 B2 | 9/2013 | Burket et al. |
| 9,181,209 B2 | 11/2015 | Fagan et al. |
| 2008/0033188 A1* | 2/2008 | Dumesic .............. C07D 307/08 549/505 |
| 2012/0157697 A1* | 6/2012 | Burket ................. C07D 307/50 549/489 |
| 2014/0309440 A1 | 10/2014 | Essayem et al. |

FOREIGN PATENT DOCUMENTS

| | | |
|---|---|---|
| CN | 102391218 A | 3/2012 |
| CN | 103261184 A | 8/2013 |
| CN | 104024238 A | 9/2014 |
| WO | WO-2012/088208 A2 | 6/2012 |
| WO | WO-2013/030131 A1 | 3/2013 |
| WO | WO-2013/138222 A1 | 9/2013 |

OTHER PUBLICATIONS

International Search Report for International Patent Application No. PCT/IB2014/066752, dated Mar. 25, 2015.

* cited by examiner

*Primary Examiner* — Taofiq A Solola
(74) *Attorney, Agent, or Firm* — Marshall, Gerstein & Borun LLP

(57) ABSTRACT

Described is a method for producing furfural from one or more substances selected from the group consisting of xylose, oligosaccharides comprising xylose units and polysaccha-rides comprising xylose units.

22 Claims, No Drawings

PRODUCTION OF FURFURAL FROM XYLOSE

CROSS-REFERENCE TO RELATED APPLICATIONS

This is the U.S. national phase of International Application No. PCT/IB2014/066752, filed Dec. 10, 2014, which claims the benefit of European Patent Application No. 13197237.4, filed Dec. 13, 2013.

The present invention relates to a method for producing furfural from one or more substances selected from the group consisting of xylose, oligosaccharides comprising xylose units and polysaccharides comprising xylose units.

Furfural is an important key substance in the chemical industry wherein it is used as the precursor of furan and derivatives of furan. Furfural is also used for the production of resins by condensation reaction of furfural with formaldehyde, phenol, acetone or urea. Furthermore, furfural is used as or in the production of a solvent, vulcanization enhancer, insecticide, fungicide, germicide and for other purposes.

Due to the finite nature and instability of fossil feedstock supply and for environmental reasons, replacement of fossil feedstock by non-fossil feedstock, i.e. feedstock obtained from renewable resources, becomes more and more important. One potential source of non-fossil feedstock for the production of furfural are substances selected from the group consisting of xylose, oligosaccharides comprising xylose units and polysaccharides comprising xylose units originating from cellulose-containing biomass. In a preferred embodiment the term 'cellulose-containing biomass' throughout this application refers to biomass containing a) cellulose as well as b) one or more substances selected from the group consisting of polyoses and other sources of xylose units. For example typical lignocellulose is cellulose-containing biomass that can serve as a source of xylose units.

Xylose is a monosaccharide also referred to as wood sugar which belongs to the group of pentoses. Oligo- and polysaccharides which comprise xylose units typically occur in plants, especially in woody parts of plants, in straw, and in the seeds or the shells of the seeds of several plants. Oligo- and polysaccharides which consist of xylose units are generally referred to as xylanes. Oligo- and polysaccharides which consist of xylose units and other monosaccharide units are generally referred to as heteroxylanes. Xylanes and heteroxylanes belong to the group of polyoses. Polyoses (earlier also referred to as hemicellulose) are polysaccharides which in plant biomass typically occur in a composite wherein said polyoses and lignin are incorporated between cellulose fibers. Dry plant biomass (water content below 15 wt.-%) which comprises cellulose, polyoses and lignin is also referred to hereinabove and hereinbelow as lignocellulose.

Methods for producing furfural from one or more substances selected from the group consisting of xylose, oligosaccharides comprising xylose units and polysaccharides comprising xylose units are known in the art. In order to maximize the furfural yield and selectivity, many of these methods rely on the technique of reactive extraction.

U.S. Pat. No. 4,533,743 A1 discloses a method wherein an aqueous solution comprising pentose, e.g. xylose, and a mineral acid, e.g. sulfuric acid or hydrochloric acid, are reacted in a plug flow reactor at a temperature between 220° C. and 300° C. Preferred is a two phase operation in which solvent is added to the reactor and furfural is recovered from the solvent by distillation.

U.S. Pat. No. 7,572,925 B2 discloses a process of making furan derivative compounds, e.g. furfural. A feedstock solution comprising a carbohydrate, e.g. xylose, is dehydrated in the presence of an acid catalyst, e.g. a mineral acid like sulfuric acid or hydrochloric acid, in a reaction vessel containing a biphasic reaction medium comprising an aqueous reaction solution and a substantially immiscible organic extraction solution. The furan derivative is extracted into the organic extraction solution. The aqueous reaction solution and/or the organic extraction solution contain at least one modifier to improve the selectivity of the process to yield furan derivative compounds. Preferably the aqueous reaction solution further comprises at least one salt, thereby yielding a saline aqueous reaction solution.

WO 2012/088208 A2 describes a method for producing furfural comprising the steps of (a) providing stillage or syrup comprising non-fermentable branched sugars e.g. xylose; (b) contacting the stillage or syrup with water to form a mixture; (c) acidifying the mixture formed in step (b) to pH 1 or less with an acid catalyst; (d) heating the mixture formed in step (c) at a temperature and for a time sufficient to convert the non-fermentable branched sugars to furfural; (e) optionally recovering the furfural thereby produced.

Preferably, said method further comprises contacting the mixture formed in step (c) with at least one water-immiscible organic solvent under suitable reaction conditions to form a mixture comprising an aqueous phase and a furfural-containing organic phase, and said step (e) of recovering furfural preferably comprises separation of the organic phase and evaporation of the organic solvent.

Typically, in the methods known in the art, substances selected from the group consisting of xylose, oligosaccharides comprising xylose units and polysaccharides comprising xylose units are treated with aggressive chemicals like strong acids (especially sulfuric acid) or oxidizing agents like nitric acid, often in combination with harsh processing conditions like temperatures of 220° C. or more. For reasons of safety, environment protection and in order to mitigate the requirements to the processing equipment with regard to corrosion stability and heat resistance, it is generally desirable to avoid or at least to reduce the use of aggressive chemicals and harsh processing conditions. Furthermore, aggressive chemicals as well as high temperatures may induce undesirable side reactions beyond the desired conversion to furfural. According to own experiments, this applies especially for sulfuric acid, which is commonly used in prior art methods for producing furfural substances selected from the group consisting of xylose, oligosaccharides comprising xylose units and polysaccharides comprising xylose units. Sulfuric acid may act as an oxidation agent and/or as a dehydrating agent, therefore undesired by-products are typically formed by coking and/or sulfatization. Formation of such by-products in turn results in reduction of the yield and selectivity of the process towards furfural, contamination of the reaction mixture and of the reaction equipment (i.e. by formation of insoluble deposits)

Accordingly it is an object of the present invention to provide a method for producing furfural from one or more substances selected from the group consisting of xylose, oligosaccharides comprising xylose units and polysaccharides comprising xylose units, which allows to reduce or even to avoid the use of aggressive chemicals like sulfuric acid and which allows to alleviate some or all of the aforementioned disadvantages of the prior art processes.

These and other objects are achieved by the method for producing furfural according to the present invention. Said method comprises the steps of providing an aqueous feed mixture comprising:
  (i) one or more substances selected from the group consisting of xylose, oligosaccharides comprising xylose units and polysaccharides comprising xylose units
  (ii) methanesulfonic acid
contacting said aqueous feed mixture with an extraction liquid comprising one or more organic solvents, wherein said one or more solvents
  have a higher solubility for furfural than said aqueous feed mixture and
  are selected so that when said aqueous feed mixture is contacted with said extraction liquid two separate liquid phases are formed, wherein in a first liquid phase the concentration of water is higher than the concentration of said organic solvents and in a second liquid phase the concentration of said organic solvents is higher than the concentration of water
wherein said aqueous feed mixture further comprises one or more salts (iii) in a concentration which is sufficient for reducing the solubility of furfural in the aqueous feed mixture and/or said salts (iii) are added after said aqueous feed mixture is contacted with said extraction liquid
subjecting said aqueous feed mixture while contacted with said extraction liquid to a thermal treatment so that said one or more substances selected from the group consisting of xylose, oligosaccharides comprising xylose units and polysaccharides comprising xylose units are reacted to furfural which is extracted from said aqueous feed mixture into said extraction liquid.

Preferably, said method comprises the steps of
providing an aqueous feed mixture comprising:
  (i) one or more substances selected from the group consisting of xylose, oligosaccharides comprising xylose units and polysaccharides comprising xylose units
  (ii) methanesulfonic acid
  (iii) one or more salts in a concentration which is sufficient for reducing the solubility of furfural in the aqueous feed mixture
contacting said aqueous feed mixture with an extraction liquid comprising one or more organic solvents, wherein said one or more solvents
  have a higher solubility for furfural than said aqueous feed mixture and
  are selected so that when said aqueous feed mixture is contacted with said extraction liquid two separate liquid phases are formed, wherein in a first liquid phase the concentration of water is higher than the concentration of said organic solvents and in a second liquid phase the concentration of said organic solvents is higher than the concentration of water
  subjecting said aqueous feed mixture while contacted with said extraction liquid to a thermal treatment so that said one or more substances selected from the group consisting of xylose, oligosaccharides comprising xylose units and polysaccharides comprising xylose units are reacted to furfural which is extracted from said aqueous feed mixture into said extraction liquid.

In one preferred embodiment the thermal treatment involves temperatures above room temperature (usually 20° C.) in combination with a pressure of 1000 kPa or more.

A related aspect of the present invention relates to the use of methanesulfonic acid in the method according to the present invention, especially in the preferred embodiments thereof as described hereinbelow.

In the present specification, the terms "oligosaccharides comprising xylose units" and "polysaccharides comprising xylose units" refer to oligosaccharides (including disaccharides) and polysaccharides, resp., the macromolecules of which comprise xylose units or consist of xylose units. The one or more substances (i) selected from the group consisting of xylose, oligosaccharides comprising xylose units and polysaccharides comprising xylose units are hereinbelow also referred to as the "educts".

In one embodiment the aqueous feed mixture useful in the methods of the invention contains amounts of organic material other than the above-defined educts, e.g. organic material selected from the group consisting of
  organic solvents for example but not limited to ethanol;
  phenolic compounds such as but not limited to lignin;
  lipids such as but not limited to lipids selected from the group consisting of oils, fatty acids and phospholipids.

In the context of this specification the feed mixture—irrespective of its content of organic material—is to be understood as an aqueous feed mixture provided that two separate liquid phases are formed when said feed mixture is contacted with said extraction liquid (as defined hereinabove and hereinbelow), wherein in a first liquid phase the concentration of water is higher than the concentration of said organic solvents and in a second liquid phase the concentration of said organic solvents is higher than the concentration of water.

As far as herein reference is made to methanesulfonic acid as a constituent of the aqueous feed mixture, the term methanesulfonic acid shall be construed to include the protonated as well as the dissociated form of methanesulfonic acid.

The pH value of the aqueous feed mixture is preferably in the range of from 0 to 4.0. In one embodiment the pH value is equal to or lower than 3.0, preferably equal to or lower than 2.0. In another embodiment the pH value is equal to or higher than 0.5. Most preferably the pH value is from 0.5 to 1.5. Preferably, in the aqueous feed solution the amount of methanesulfonic acid is adjusted so that the pH is in the above-specified range.

Methanesulfonic acid ($CH_3SO_2(OH)$, sometimes abbreviated as MSA) is commercially available e.g. as an aqueous solution comprising 70 wt.-% of methanesulfonic acid (e.g. from BASF SE, Carl-Bosch-Str. 38, 67056 Ludwigshafen, Germany as Lutropur® MSA) and in anhydrous form (e.g. from BASF SE, Carl-Bosch-Str. 38, 67056 Ludwigshafen, Germany as Lutropur® MSA100). Methanesulfonic acid is infinitely soluble in water and has a pKa of −1.9 which is considerably lower than the pKa of the first stage of dissociation of sulfuric acid (−3 for the first stage of dissociation, 1.9 for the second stage of dissociation). Accordingly, methanesulfonic acid is a less strong acid than sulfuric acid.

Methanesulfonic acid has a lower corrosivity in comparison to sulfuric acid, nitric acid, hydrochloric acid, and in contrast to sulfuric acid and nitric acid it does not act as an oxidizing and/or dehydrating agent. According to own experiments, formation of undesired by-products, e.g. by coking of the educts is avoided and the yield of the target product furfural is increased.

A further advantage of methanesulfonic acid over sulfuric acid is that methanesulfonic acid is a significantly less strong sulfonation agent than sulfuric acid. According to own experiments soap-like products are formed in a lower amount, and phase separation is faster and more efficient.

Moreover, most salts of methanesulfonic acid are easier soluble in water than salts of sulfuric acid, so that problems due to formation of insoluble deposits are reduced.

A further advantage of methanesulfonic acid is its biodegradability both under aerobic and anaerobic conditions.

Despite these advantages of methanesulfonic acid, typically mineral acids are used for chemical reactions which require an acidic medium.

In the method of the present invention, said aqueous feed mixture is subjected to a thermal treatment, i.e. is exposed to an increased temperature (compared to usual room temperature of 20° C.), to facilitate the reaction of said educts into furfural.

While being subject to a thermal treatment so that said educts are reacted to furfural, said aqueous feed mixture is in contact with an extraction liquid comprising one or more organic solvents having (i.e. providing) a higher solubility for furfural than said aqueous feed mixture (i.e. furfural has a higher solubility in the one or more organic solvents than in said aqueous feed mixture). In the context of the present application the term solvent in each case denotes an individual chemical compound.

Said one or more organic solvents are selected so that when said aqueous feed mixture is contacted with said extraction liquid two separate liquid phases are formed, wherein in a first liquid phase of said two separate liquid phases the concentration of water is higher than the concentration of said organic solvents and in a second liquid phase of said two separate liquid phases the concentration of said organic solvents is higher than the concentration of water. Preferably, at the time of being contacted with said aqueous feed liquid, the extraction liquid used in the method of the present invention consists of one or more organic solvents.

Said first and second liquid phase may coexist in the form of two continuous phases or in the form of a disperse system, e.g. an emulsion, wherein said second liquid phase (as defined above) is dispersed within said first phase (as defined above) in such manner that the second phase is present in the form of a multitude of droplets.

Due to the higher solubility of furfural in said one or more organic solvents, the formed furfural is extracted from said aqueous feed mixture into said extraction liquid, i.e. from said first liquid phase wherein the concentration of water is higher than the concentration of said organic solvents into said second liquid phase wherein the concentration of said organic solvents is higher than the concentration of water. By extraction into said extraction liquid furfural is removed from said aqueous feed mixture wherein one or more substances selected from the group consisting of xylose, oligosaccharides comprising xylose units and polysaccharides comprising xylose units are reacting. Doing so is advantageous because in the presence of xylose the reaction product furfural may undergo undesired side reactions which result in a reduction of the selectivity and the yield of the reaction with regard to furfural. Preferably, the formed furfural is continuously extracted, preferably over the whole duration of the thermal treatment of the aqueous feed mixture.

Preferably, in the method of the present invention and in its preferred embodiments, said one or more solvents are selected so that the solubility of furfural in said solvents exceeds the solubility of furfural in said aqueous feed mixture at the same temperature by 10% or more, preferably by 50% or more, and most preferably by 80% or more.

The aqueous feed mixture used in the method of the present invention comprises one or more salts in a concentration which is sufficient for reducing the solubility of furfural in the aqueous feed mixture, compared to the solubility of furfural at the same temperature in an aqueous feed mixture which does not comprise any of the one or more salts (iii) but otherwise is of identical composition. In the aqueous feed mixture used in the method of the present invention, at least during the thermal treatment said one or more salts are present in the dissociated form so that at least one kind of cations different from hydrogen cations and at least one kind of anions different from hydroxide anions are present. The presence of electrolytes like salts in an aqueous mixture further comprising one or more non-dissociated substances (like furfural) reduces the solubility of said non-dissociated substances in the water of said aqueous mixture. This phenomenon is known as the salt effect or as "salting out". Thus, due to the presence of one or more salts in the aqueous feed mixture, the transfer of the formed furfural into the extraction liquid is promoted.

In the aqueous feed mixture used in the method of the present invention the concentration of said one or more salts (iii) is preferably selected so that the solubility of furfural is reduced by 10% or more, preferably by 50% or more, and most preferably by 80% or more, compared to the solubility of furfural at the same temperature in an aqueous feed mixture which does not comprising any of the one or more salts (iii) but otherwise is of identical composition.

Preferably, in the method of the present invention and in its preferred embodiments the step of thermal treatment is conducted in a manner so that 80% by weight or more, preferably 90% by weight or more of said one or more salts (iii) provided in the aqueous feed mixture can be recovered. This is achieved by appropriately selecting the one or more salts (iii) in such manner that they are substantially non-reactive, i.e. only a minor fraction (20 wt.-% or less) of the amount of said salts (iii) provided in the aqueous feed mixture undergoes chemical changes during the thermal treatment. Thus, a major fraction (80 wt.-% or more, preferably 90 wt.-% or more) of the amount of said one or more salts (iii) which is present in the aqueous feed mixture as provided is capable of being recovered after the thermal treatment. In each case the term "the aqueous feed mixture as provided" refers to the composition of the aqueous feed mixture immediately before the steps of contacting said aqueous feed mixture with said extraction liquid and subjecting said aqueous feed mixture while contacted with said extraction liquid to a thermal treatment.

Preferably, said one or more salts (iii) are selected from the group consisting of salts comprising a cation selected from the group consisting of cations of metals of groups I and II and an anion selected from the group consisting of chloride, bromide, iodide, methanesulfonate, toluenesulfonate, phosphate, tetrafluoroborate, trifluormethansulfonate, acetate and nitrate. Preferred anions are chloride, methanesulfonate and toluenesulfonate.

The metals of groups I and II, resp., of the periodic system of elements are also commonly referred to as alkali metals and alkaline earth metals, resp.

Salts comprising the above-mentioned cations and anions are usually substantially non-reactive, i.e. a major fraction (80 wt.-% or more, preferably 90 wt.-% or more) of the amount of said salts (iii) which is present in the aqueous feed mixture as provided (i.e. before the steps of contacting said aqueous feed mixture with said extraction liquid and subjecting said aqueous feed mixture while contacted with said extraction liquid to a thermal treatment) is capable of being recovered after the thermal treatment.

Further preferably the aqueous feed mixture comprises two or more salts (iii), said two or more salts preferably comprising one salt selected from the group consisting of alkali metal chlorides and one salt selected from the group of alkali metal salts of methanesulfonic acid.

Thus, in a preferred embodiment of the method of the present invention, the aqueous feed mixture comprises methane sulfonic acid besides one salt selected from the group of alkali metal salts of methanesulfonic acid. Thus, at least when said alkali metal salt of methanesulfonic acid is fully dissociated the concentration of methane sulfonated anions in the aqueous feed mixture is larger than the concentration of hydrogen ions.

Preferably, the weight ratio of sodium chloride to sodium methanesulfonate is in the range of from 10:1 to 1:10, preferably from 5:1 to 1:5; more preferably from 2:1 to 1:2 and especially preferably from 1.5:1 to 1:1.5 and most preferably from 1.2:1 to 1:1.2, In own experiments, said salts have been found to perform best with regard to solubility in the aqueous feed mixture, reduction of the solubility of furfural, and chemical stability. When salts having methanesulfonate anion are substituted by salts having iodide anion there is some risk that iodine is formed during the thermal treatment which accumulates in the second liquid phase. Thus with iodide anions the loss of salts (iii) may be increased compared to salts having methanesulfonate anions, which essentially remain stable during the thermal treatment and are only to a minor extent transferred into the second liquid phase. Furthermore, due to the transfer of iodine into the second liquid phase, said second liquid phase contains iodide as a contaminant which disturbs recovery of the target product furfural from said second liquid phase.

Preferably, in the aqueous feed mixture the total amount of further acids selected from the group consisting of mineral acids (sulfuric acid, nitric acid, hydrochloric acid and phosphoric acid) is 100 wt.-% or less, preferably 50 wt.-% or less and more preferably 10 wt.-% or less, based on the weight of the methanesulfonic acid present in the aqueous feed mixture. However, in order to reduce the use of aggressive chemicals, which may cause the above-mentioned problems regarding safety, corrosion and formation of side products, it is preferred that the aqueous feed mixture does not contain more than 1 wt.-% sulfuric acid, based on the weight of the methanesulfonic acid present in the aqueous feed mixture, and does not contain any other mineral acid.

Particularly preferably, the aqueous feed mixture consists of (i) one or more substances selected from the group consisting of xylose, oligosaccharides comprising xylose units and polysaccharides comprising xylose units,
(ii) methanesulfonic acid,
(iii) one or more salts in a concentration which is sufficient for reducing the solubility of furfural in the aqueous feed mixture, wherein preferably said salts are selected according to the preferred embodiments explained above
(iv) water and
(v) optionally sulfuric acid, wherein the amount of sulfuric acid in the aqueous feed mixture is not more than 1 wt.-% of sulfuric acid based on the weight of the methanesulfonic acid present in the aqueous feed mixture.

In a preferred method of the present invention, in said aqueous feed mixture the total concentration of (i) said one or more substances selected from the group consisting of xylose, oligosaccharides comprising xylose units and polysaccharides comprising xylose units is in the range of from 1 wt.-% to 70 wt.-%, preferably of from 10 wt.-% to 40 wt.-% further preferably of from 20 wt.-% to 30 wt.-% based on the total weight of said aqueous feed mixture. When the concentration of (i) said educts is below 1 wt.-%, the method typically becomes inefficient, because a very large volume of liquids is handled for obtaining a comparatively small amount of furfural. When the concentration of (i) said educts is above 70 wt.-%, the aqueous feed mixture typically becomes very viscous and accordingly difficult to handle.

In another preferred method of the present invention, in said aqueous feed mixture the concentration of (ii) methanesulfonic acid is in the range of from 0.1 wt.-% to 5 wt.-%, preferably of from 1 wt.-% to 3 wt.-% further preferably of from 1.5 wt.-% to 2.5 wt.-% based on the total weight of said aqueous feed mixture. When the concentration of (ii) methanesulfonic acid is below 0.1 wt.-%, the amount of methanesulfonic acid typically has no significant effect on the yield of furfural, compared to a method for producing furfural wherein all conditions and compositions are identical with the sole exception that the aqueous feed mixture does not comprise methanesulfonic acid. When the concentration of (ii) methanesulfonic acid is above 5 wt.-% the risk of undesirable extraction of methanesulfonic acid into the extraction liquid is considerable.

In another preferred method of the present invention, in said aqueous feed mixture the total concentration of (iii) said one or more salts (as defined above) is in the range of from 0.5 wt.-% to 35 wt.-%, preferably of from 5 wt.-% to 30 wt.-%, further preferably of from 10 wt.-% to 25 wt.-% most preferably of from 15 wt.-% to 20 wt.-% based on the total weight of said aqueous feed mixture. When the concentration of (iii) said one or more salts (as defined above) is below 0.5 wt.-%, typically no significant reduction of the solubility of furfural is achieved, compared to an aqueous feed mixture not comprising any salts (iii) but being of otherwise identical composition. When the concentration of (iii) said one or more salts (as defined above) is above 35 wt.-%, the method becomes typically inefficient, because a very large amount of salts (iii) is employed for obtaining a comparatively small amount of furfural. Furthermore, according to own experiments such large amounts of salts (iii) in some cases have been found to reduce the selectivity and yield of the reaction towards furfural.

In an especially preferred method of the present invention, in said aqueous feed mixture the total concentration of (i) said one or more substances selected from the group consisting of xylose, oligosaccharides comprising xylose units and polysaccharides comprising xylose units is in the range of from 1 wt.-% to 70 wt.-%, preferably of from 10 wt.-% to 40 wt.-%, further preferably of from 20 wt.-% to 30 wt.-% and the concentration of (ii) methanesulfonic acid is in the range of from 0.1 wt.-% to 5 wt.-%, preferably of from 1 wt.-% to 3 wt.-%, further preferably of from 1.5 wt.-% to 2.5 wt.-% and the total concentration of (iii) said one or more salts is in the range of from 0.5 wt. % to 35 wt.-%, preferably of from 5 wt.-% to 30 wt.-%, further preferably of from 10 wt.-% to 25 wt.-% most preferably of from 15 wt.-% to 20 wt.-% wherein the concentration in each case is based on the total weight of said aqueous feed mixture.

Preferably in said aqueous feed mixture the total concentration of yeast cells is $120*10^6$ cells/ml or less, preferably $100*10^6$ cells/ml or less, further preferably $80*10^6$ cells/ml or less, more preferably $60*10^6$ cells/ml or less, $50*10^6$ cells/ml or less, $40*10^6$ cells/ml or less, $30*10^6$ cells/ml or less, $20*10^6$ cells/ml or less, $15*10^6$ cells/ml or less, especially preferably $10*10^6$ cells/ml or less, $9*10^6$ cells/ml or less, $8*10^6$ cells/ml or less, $7*10^6$ cells/ml or less, $6*10^6$ cells/ml or less, most preferably $5*10^6$ cells/ml or less.

Further preferably, in said aqueous feed mixture the total concentration of yeast cells in the form of living cells and spores is $120*10^6$ cells/ml or less, preferably $100*10^6$ cells/ml cells/ml or less, further preferably $80*10^6$ cells/ml or less, more preferably $60*10^6$ cells/ml or less, $50*10^6$ cells/ml or less, $40*10^6$ cells/ml or less, $30*10^6$ cells/ml or less, $20*10^6$ cells/ml or less, $15*10^6$ cells/ml or less, $10*10^6$ cells/ml or less, $9*10^6$ cells/ml or less, $8*10^6$ cells/ml or less, $7*10^6$ cells/ml or less, $6*10^6$ cells/ml or less, most preferably $5*10^6$ cells/ml or less.

The term yeast cells refers to cells which are capable of catalyzing the alcoholic fermentation, e.g. (but not limited to) Saccharomycetaceae like those selected from the group consisting of *Saccharomyces cerevisiae* and *Schizosaccharomyces pombe*.

A low concentration of yeast cells in the aqueous feed mixture has the advantage that the extent of undesired side reactions and formation of undesired by-products is reduced, resulting in an increased yield and selectivity of the reaction with regard to furfural.

Especially preferred is a method of the invention wherein two or more, preferably all of the above-described preferred features regarding the composition of the aqueous feed mixture are combined.

The one or more organic solvents in said extraction liquid are preferably selected from the group consisting of solvents which (i) have a boiling point which is below the boiling point of furfural wherein in each case the boiling point is the boiling point at a pressure of 1000 hPa and (ii) do form an azeotropic mixture with furfural. The boiling point of furfural at a pressure of 1000 hPa is 162° C. Selecting the one or more organic solvents in said extraction liquid as defined above has the advantage that said solvents can typically be separated from the target product furfural by distillation without subjecting the furfural to such a high thermal load as it would be inevitably the case when the one or more organic solvents in said extraction liquid had a higher boiling point than furfural so that the furfural has to be distilled-off from the solvents. Furthermore, when the boiling point of the liquid which has to be distilled is low, the amount of thermal energy required for the distillation is low which is preferred for economical and ecological reasons.

Preferably, at the time of being contacted with said aqueous feed liquid, the extraction liquid used in the method of the present invention consists of one or more organic solvents having a boiling point which is below the boiling point of furfural wherein in each case the boiling point is the boiling point at a pressure of 1000 hPa.

Preferably in said extraction liquid said one or more solvents are selected from the group consisting of tetrahydrofurane, methyl tetrahydrofurane and dimethyl tetrahydrofurane.

In the step of contacting said aqueous feed mixture with said extraction liquid the weight ratio of said aqueous feed mixture to said extraction liquid is in the range of from 95:5 to 5:95, preferably from 80:20 to 20:80, further preferably from 60:40 to 50:50.

Especially preferred is a method of the invention wherein two or more, preferably all of the above-described preferred features regarding the composition of the aqueous feed mixture and the composition of the extraction liquid are combined.

The thermal treatment of the aqueous feed mixture in contact with the extraction liquid is carried out at a temperature in the range of from 80° C. to 250° C., preferably from 130° C. to 220° C., further preferably of from 150° C. to 180° C. at a pressure in the range of from 100 kPa to 3000 kPa, preferably from 1000 to 2500 kPa wherein the pressure and the temperature are selected so that said coexisting first and second liquid phases are maintained, for a duration of from 1 seconds to 6 hours, preferably of from 5 seconds to 3 hours, further preferably from 100 seconds to 30 minutes and even more preferably from 100 seconds to 300 seconds.

Optionally, after completion of the thermal treatment, the two coexisting liquid phases are allowed to cool and/or the pressure is lowered, before the coexisting liquid phases are separated. Preferably, the two coexisting liquid phases are allowed to cool and/or the pressure is lowered, and then the coexisting liquid phases are separated.

When the temperature is below 80° C., the yield of furfural is too low. When the temperature is above 250° C., the amount of undesirable by-products is too high. In one embodiment, for economical and ecological reasons the temperature of the thermal treatment is preferably as low as possible. In a preferred embodiment the temperature of the thermal treatment is selected so that the optimal selectivity of the reaction and/or the optimal yield of furfural is achieved.

Regarding the selection of the pressure, it is important that the pressure is sufficiently high so as to maintain said coexisting first liquid phase and said second liquid phase at the selected temperature. On the other hand, for economical and technical reasons the pressure is preferably as low as possible.

When the duration of the thermal treatment is below 1 second, the method becomes inefficient because only a low amount of furfural is formed. When the duration of the thermal treatment is above 6 hours, it becomes difficult to maintain continuous extraction of the furfural, resulting in losses of furfural yield. Moreover, for economical and ecological reasons the duration of the thermal treatment is preferably as short as possible.

During the thermal treatment, in the first liquid phase the concentration of said educts (i) decreases due to conversation into furfural, and in the second liquid phase, the concentration of furfural increases due to extraction of the formed furfural from the first liquid phase into the second liquid phase.

Preferably, at least during the thermal treatment said first and second liquid phase exist in the form of a disperse system, e.g. an emulsion, wherein said second liquid phase (as defined above) is dispersed within said first phase (as defined above) in such manner that the second phase is present in the form of a multitude of droplets. Carrying out the reaction in a disperse system of the two phases has the advantage of increasing the interface between the two phases, so that transfer of furfural from the first liquid phase into the second liquid phase is facilitated. This is achieved by intensively mixing the two liquid phases, e.g. by means of stirring. Preferably the mixing, e.g. stirring, action is continued throughout the whole duration of the thermal treatment. After completion of the thermal treatment, the mixing, e.g. stirring, action is stopped to allow formation of two continuous phases, thus facilitating separation of said two phases.

It is assumed that when the aqueous feed mixture comprises one or more substances selected from the group consisting of oligosaccharides comprising xylose units and polysaccharides comprising xylose units xylose is formed from said substances, and the formed xylose is subsequently reacted to furfural.

Preferred is a method of the invention wherein two or more, preferably all of the above-described preferred features regarding the conditions of the thermal treatment are combined.

Further preferred is a method of the invention wherein two or more, preferably all of the above-described preferred features regarding the conditions of the thermal treatment, the composition of the aqueous feed mixture and the composition of the extraction liquid are combined.

In this regard especially preferred is a method according to the present invention wherein
the aqueous feed mixture comprises
(i) said one or more substances selected from the group consisting of xylose, oligosaccharides comprising xylose units and polysaccharides comprising xylose units in a total concentration of from 1 wt.-% to 70 wt.-%, preferably of from 10 wt.-% to 40 wt.-%, further preferably of from 20 wt.-% to 30 wt.-%
(ii) methanesulfonic acid in a concentration of from 0.1 to 5 wt.-%, preferably of from 1 wt.-% to 3 wt.-% further preferably of from 1.5 wt.-% to 2.5 wt.-%
(iii) both salts selected from the group consisting of sodium chloride and sodium methanesulfonate, wherein the total concentration of sodium chloride and sodium methanesulfonate is in a range of from 0.5 wt. % to 35 wt.-%, preferably of from 5 wt.-% to 30 wt.-%, further preferably of from 10 wt.-% to 25 wt.-% most preferably of from 15 wt.-% to 20 wt.-% and the weight ratio of sodium chloride to sodium methanesulfonate is in the range of from 10:1 to 1:10, preferably from 5:1 to 1:5; more preferably from 2:1 to 1:2 especially preferably from 1.5:1 to 1:1.5 and most preferably from 1.2:1 to 1:1.2,
wherein the concentration in each case is based on the total weight of the aqueous feed mixture;
the extraction liquid consists of methyl tetrahydrofurane and optionally one or more further constituents;
in the step of contacting said aqueous feed mixture and said extraction liquid the weight ratio of said aqueous feed mixture to said extraction liquid is in the range of from 95:5 to 5:95, preferably from 80:20 to 20:80, preferably from 60:40 to 50:50,
the thermal treatment the aqueous feed mixture in contact with the extraction liquid is carried out at a temperature in the range of from 130° C. to 220° C., preferably of from 150° C. to 180° C. for a duration of from 1 to 10 minutes at a pressure in the range of from 1200 kPa to 2000 kPa,
wherein the pressure and the temperature are selected so that said coexisting first and second liquid phases are maintained.

In preferred embodiments of the method of the present invention, a furfural yield of 75% or more, preferably of 80% or more, based on the weight of xylose units in the educts, is achieved. Methods to determine the amount and weight of the xylose units in the educts are known in the art.

Generally, in the method according to the present invention, the origin of the educts, i.e. said one or more substances selected from the group consisting of xylose, oligosaccharides comprising xylose units and polysaccharides comprising xylose units, is not critical. However, for economical and ecological reasons, it is preferred that said educts originate from renewable resources like biomass, e.g. plant biomass.

This is achieved by a preferred method according to the present invention which further comprises the steps of
processing cellulose-containing biomass, preferably lignocellulose, so that said one or more substances selected from the group consisting of xylose, oligosaccharides comprising xylose units and polysaccharides comprising xylose units are formed, and
preparing said aqueous feed mixture comprising:
(i) said formed one or more substances selected from the group consisting of xylose, oligosaccharides comprising xylose units and polysaccharides comprising xylose units
(ii) methanesulfonic acid
(iii) one or more salts in a concentration which is sufficient for reducing the solubility of furfural in the aqueous feed mixture.

Biomass is a general term for the whole organic matter produced by the growth and metabolism of all kinds living organisms, i.e. micro-organisms, plants, animals and humans. A major source of biomass is photosynthesis performed by plants.

Cellulose-containing biomass which is suitable as a source for the educts of the method of the present invention may be selected from the group consisting of plant biomass, agricultural wastes, forestry residues, sugar processing residues, paper waste and blends thereof. For economical and ecological reasons, cellulose-containing biomass in the form of wastes and residues is especially preferably. As mentioned above, dry plant biomass (water content below 15 wt.-%) comprises as main components cellulose, polyoses and lignin.

Methods for processing cellulose-containing biomass to obtain said one or more substances selected from the group consisting of xylose, oligosaccharides comprising xylose units and polysaccharides comprising xylose units are generally known in the art. Said step of processing cellulose-containing biomass is assumed to involve the breaking of a tight, stable composite comprising cellulose, polyoses (e.g. xylanes) and lignin. This is typically achieved by chemical, physical, enzymatic or microbial techniques or combinations thereof.

Especially preferred is a method wherein in said step of processing cellulose-containing biomass a treatment mixture comprising cellulose-containing biomass, water and methanesulfonic acid is subjected to a temperature in the range of from 100° C. to 210° C., preferably of from 130° C. to 195° C., further preferably of from 150° C. to 180° C., at a pressure in the range of from 100 to 3000 kPa preferably from 1000 to 2000 kPa wherein the pressure is selected so that at least a part of the water is in the liquid state. Further details of said specific technique of processing cellulose-containing biomass are disclosed in the European patent application 13187189.9 which is incorporated herein by reference. Especially preferred are the preferred methods of processing cellulose-containing biomass disclosed in the European patent application 13187189.9. A specific advantage of this method is that as a result of the step of processing cellulose-containing biomass a liquid phase consisting of an aqueous solution which comprises (i) xylose and (ii) methanesulfonic acid is obtained from which by addition of one or more salts (iii) as defined above an aqueous feed mixture for the method of the present invention can be prepared.

Alternatively, the aqueous feed mixture may be prepared by
adding (ii) methanesulfonic acid and (iii) one or more salts as defined above to an aqueous mixture comprising (i) one or more substances selected from the group consisting of xylose, oligosaccharides comprising xylose units and polysaccharides comprising xylose units obtained by processing cellulose-containing biomass, preferably lignocellulose, wherein preferably no further purification of the aqueous mixture comprising (i) one or more substances selected from the group consisting of xylose, oligosaccharides comprising xylose units and polysaccharides comprising xylose units obtained by processing cellulose-containing biomass is needed
or
providing one or more substances selected from the group consisting of xylose, oligosaccharides comprising xylose units and polysaccharides comprising xylose units in solid form and preparing an aqueous mixture comprising (i) said one or more substances selected from the group consisting of xylose, oligosaccharides comprising xylose units and polysaccharides comprising xylose units, (ii) methanesulfonic acid and (iii) one or more salts as defined above.

Processing of biomass is often carried out in a biorefinery. A biorefinery is a facility for the conversion of biomass into one or more of fuels, power, heat, and value-added chemicals. The biorefinery concept is in some manner analogous to a common petroleum refinery which produces multiple fuels and products from petroleum. Typically, in a biorefinery cellulose-containing biomass, preferably lignocellulose is separated into lignin, polyoses (which are optionally further converted into the corresponding monosaccharides like xylose) and cellulose (which is optionally further converted into the corresponding monosaccharides like glucose). Preferably as feedstock for a biorefinery such kinds of biomass are used which are not in competition with the production of food, and which can be exploited without damaging the natural vegetation. This approach is also referred to as a second generation biorefinery. Preferred feedstock of such a second generation biorefinery is selected from agricultural wastes (e.g. straw), non-food plant material and forestry residues.

Especially preferred is a method of the invention wherein two or more, preferably all of the above-described preferred features regarding the conditions of processing the cellulose-containing biomass, the conditions of the thermal treatment, the composition of the aqueous feed mixture and the composition of the extraction liquid are combined.

For economical and ecological reasons, it is desirable that substances like solvents and auxiliary agents which do not undergo chemical changes during the thermal treatment of the method of the present invention are recycled. Accordingly, an especially preferred method of the present invention further comprises after completion of the thermal treatment one or both of the steps of
recovering from the first liquid phase an aqueous mixture comprising methane sulfonic acid (ii) and said one or more salts (iii) and using said recovered aqueous mixture for replenishing said aqueous feed mixture
and/or
recovering from said second liquid phase said one or more organic solvents and using said recovered one or more organic solvents for replenishing said extraction liquid.

Preferably, an aqueous mixture comprising methane sulfonic acid (ii) and said one or more salts (iii) is recovered from the first liquid phase and said recovered aqueous mixture is used for replenishing said aqueous feed mixture, and one or more organic solvents are recovered from said second liquid phase and said recovered one or more organic solvents are used for replenishing said extraction liquid.

More specifically, the aqueous feed mixture is preferably replenished by recovering after completion of the thermal treatment from said first liquid phase an aqueous mixture comprising said methane sulfonic acid (ii) and said one or more salts (iii), and adding (i) said one or more substances selected from the group consisting of xylose, oligosaccharides comprising xylose units and polysaccharides comprising xylose units to said recovered aqueous mixture. It is noted that after the thermal treatment non-reacted fractions of the educts, non-extracted furfural and by-products formed during the thermal treatment may be present in first liquid phase.

More specifically the extraction liquid is preferably replenished by recovering after completion of the thermal treatment from said second liquid phase said one or more organic solvents and preparing an extraction liquid using said recovered one or more organic solvents. Preferably, said one or more organic solvents in said extraction liquid are selected from the group consisting of solvents having a boiling point which is below the boiling point of furfural, so that said one or more solvents can be separated from said second liquid phase by distillation.

Especially preferred is a method of the invention wherein two or more, preferably all of the above-described preferred features regarding the conditions of processing the cellulose-containing biomass, the conditions of the thermal treatment, the composition of the aqueous feed mixture and the composition of the extraction liquid and the recovering of an aqueous mixture comprising methane sulfonic acid (ii) and said one or more salts (iii) and/or the recovering of one or more organic solvents are combined.

Also disclosed herein is a method to obtain 5-(hydroxymethyl)furfural (hereinbelow referred to as HMF) from C6 sugars (hexoses; aldohexoses and/or ketohexoses), oligosaccharides comprising hexose units and/or polysaccharides comprising hexose units. Suitable hexoses for conversion to HMF by the method of the present invention are (without being limited thereto) fructose, glucose, mannose, galactose, sorbose, or combinations thereof, most preferably fructose, glucose, or combinations thereof.

The method for producing HMF according to the present invention comprises the steps of
providing an aqueous feed mixture comprising:
(i) one or more substances selected from the group consisting of hexose, oligosaccharides comprising hexose units and polysaccharides comprising hexose units, wherein the hexose or hexose unit is preferably fructose or glucose, preferably the one or more substances are fructose, glucose or combinations thereof,
(ii) methanesulfonic acid
contacting said aqueous feed mixture with an extraction liquid comprising one or more organic solvents, as described herein, wherein said one or more solvents
have a higher solubility for HMF than said aqueous feed mixture and
are selected so that when said aqueous feed mixture is contacted with said extraction liquid two separate liquid phases are formed, wherein in a first liquid phase the concentration of water is higher than the concentration of said organic solvents and in a second liquid phase the concentration of said organic solvents is higher than the concentration of water
wherein said aqueous feed mixture further comprises one or more salts (iii), as described herein, in a concentration which is sufficient for reducing the solubility of HMF in the aqueous feed mixture and/or said salts (iii) are added after said aqueous feed mixture is contacted with said extraction liquid
subjecting said aqueous feed mixture while contacted with said extraction liquid to a thermal treatment so that said one or more substances selected from the group consisting of hexose, oligosaccharides comprising hexose units and polysaccharides comprising hexose units, wherein the hexose or hexose unit is preferably fructose or glucose, are reacted to HMF which is extracted from said aqueous feed mixture into said extraction liquid.

Preferably, said method comprises the steps of providing an aqueous feed mixture comprising:
(i) one or more substances selected from the group consisting of hexose, oligosaccharides comprising hexose units and polysaccharides comprising hexose units, wherein the hexose or hexose unit is preferably fructose or glucose, preferably the one or more substances are fructose, glucose or combinations thereof,
(i) methanesulfonic acid
(iii) one or more salts, as described herein, in a concentration which is sufficient for reducing the solubility of HMF in the aqueous feed mixture
contacting said aqueous feed mixture with an extraction liquid comprising one or more organic solvents, as described herein, wherein said one or more solvents have a higher solubility for HMF than said aqueous feed mixture and
are selected so that when said aqueous feed mixture is contacted with said extraction liquid two separate liquid phases are formed, wherein in a first liquid phase the concentration of water is higher than the concentration of said organic solvents and in a second liquid phase the concentration of said organic solvents is higher than the concentration of water
subjecting said aqueous feed mixture while contacted with said extraction liquid to a thermal treatment so that said one or more substances selected from the group consisting of hexose, oligosaccharides comprising hexose units and polysaccharides comprising hexose units, wherein the hexose or hexose unit is preferably fructose or glucose, are reacted to HMF which is extracted from said aqueous feed mixture into said extraction liquid, as described herein.

Preferably, in said method the aqueous feed mixture comprising one or more hexoses, oligosaccharides comprising one or more hexose units and polysaccharides comprising one or more hexose units or combinations thereof also comprises xylose, oligosaccharides comprising xylose units and polysaccharides comprising xylose units, or combinations thereof, preferably wherein the xylose or xylose unit is converted to furfural and the one or more hexose or hexose unit is converted to HMF. Preferably, any furfural produced is converted to HMF in additional steps.

EXAMPLES

In a basic series of experiments (tables 1-6 below) pure crystalline xylose was used as the educt. Acidic solutions of the educt were prepared by dissolving approximately 250 mg of xylose in an aqueous solution of methanesulfonic acid (MSA) in a reaction vessel equipped with a magnet stirrer.

For comparison experiments, acidic solutions were prepared by dissolving samples of crystalline xylose in an aqueous solution comprising of sulfuric acid.

The concentration of xylose and acid (either methanesulfonic acid or sulfuric acid) in said acidic solutions of the educt is indicated for each sample in tables 1-6 hereinbelow.

To said acidic solutions of the educt, one or more salts selected from the group consisting of sodium chloride, sodium methanesulfonate and sodium iodide were added in the amounts indicated for each sample in the tables 1-6 hereinbelow. For comparison experiments, to some samples of acidic solutions of the educt no salt was added.

The aqueous solutions comprising xylose as the educt, either sulfuric or methanesulfonic acid and either no additional salt or one or more salts selected from the group consisting of sodium chloride, sodium methanesulfonate and sodium iodide were used as aqueous feed mixtures for the production of furfural.

After the added salt(s) were dissolved, the aqueous feed mixture in each reaction vessel was superimposed by an amount of methyl-tetrahydrofurane (Me-THF) as the extraction liquid specified in the tables 1-6 hereinbelow.

The reaction vessels were placed in a microwave apparatus and the samples were subjected to a thermal treatment by heating to the target temperatures indicated for each sample in the tables 1-6 hereinbelow and holding the samples at the target temperature at a pressure of 1600 kPa for a duration (holding time) indicated for each sample in the tables 1-6 hereinbelow. The time to reach the target temperature was 48 seconds, starting from 20° C.

After completion of the thermal treatment at the target temperature the samples were cooled to room temperature by means of a pressurized air jet. The aqueous phase (first liquid phase) and the phase of the extraction liquid (second liquid phase) were separated, and their respective weight was determined and the respective concentrations of xylose and furfural were analyzed by means of HPLC.

The degree of conversation of xylose as well as the yield and the selectivity respective to furfural are given in tables 1-6 hereinbelow.

TABLE 1

| Sample no. | 1 | 2 | 3 | 4 | 5 | 6 | 7 |
|---|---|---|---|---|---|---|---|
| Target temperature [° C.] | 160 | 160 | 160 | 160 | 170 | 170 | 170 |
| holding time at target temperature [min] | 5 | 5 | 10 | 10 | 5 | 5 | 10 |
| Xylose feed in % | 5 | 5 | 5 | 5 | 5 | 5 | 5 |
| Kind of acid | MSA | H2SO4 | MSA | H2SO4 | MSA | H2SO4 | MSA |
| acid concentration in wt.-% | 2 | 2 | 2 | 2 | 2 | 2 | 2 |
| Weight of superimposed Me—THF [mg] | 10004 | 9989 | 9993 | 10005 | 10007 | 9997 | 10010 |
| Degree of conversation of xylose [%] | 70.7 | 61.49 | 76.3 | 83.98 | 89.2 | 86.87 | 100 |
| furfural yield [%] | 40.1 | 40.35 | 49.5 | 58.43 | 56.9 | 56.55 | 64.2 |
| selectivity for furfural [%] | 56.7 | 65.62 | 64.8 | 69.57 | 63.8 | 65.1 | 64.2 |

TABLE 2

| Sample no. | 8 | 9 | 10 | 11 | 12 | 13 |
|---|---|---|---|---|---|---|
| Target temperature [° C.] | 160 | 160 | 160 | 160 | 170 | 170 |
| holding time at target temperature [min] | 5 | 5 | 10 | 10 | 5 | 5 |
| Xylose feed in % | 5 | 4.81 | 5 | 4.81 | 5 | 4.77 |
| Kind of acid | MSA | H2SO4 | MSA | H2SO4 | MSA | H2SO4 |
| acid concentration in wt.-% | 2 | 2 | 2 | 2 | 2 | 2 |
| Weight of superimposed Me—THF [mg] | 10004 | 10003 | 9998 | 9989 | 9999 | 9992 |
| Amount of added NaCl [mg] | 508 | 507 | 513 | 505 | 509 | 502 |
| Degree of conversation of xylose [%] | 87.2 | 88.21 | 93.5 | 100 | 100 | 100 |
| furfural yield [%] | 63.8 | 63.48 | 69.8 | 67.34 | 66.58 | 70.01 |
| selectivity for furfural [%] | 73.1 | 71.97 | 74.6 | 67.34 | 66.58 | 70.01 |

TABLE 3

| Sample no. | 14 | 15 | 16 | 17 | 18 |
|---|---|---|---|---|---|
| Target temperature [° C.] | 180 | 180 | 180 | 180 | 180 |
| Duration of holding at target temperature [min] | 5 | 5 | 5 | 5 | 5 |
| Xylose feed in % | 4.8 | 4.75 | 4.82 | 4.83 | 4.75 |
| Kind of acid | MSA | MSA | MSA | MSA | MSA |
| acid concentration in wt.-% | 2 | 2 | 2 | 2 | 2 |
| Weight of superimposed Me—THF [mg] | 10014 | 10019 | 10016 | 10001 | 10001 |
| Amount of added NaCl [mg] | 507 | 401 | 252 | 253 | 0 |
| Amount of added NaI ([mg] | 0 | 102 | 250 | 0 | 0 |
| Amount of added Na-methansulfonate [mg] | 0 | 0 | 0 | 251 | 250 |
| Degree of conversation of xylose [%] | 100 | 94.6 | 95.2 | 95.5 | 82.1 |
| furfural yield [%] | 36.4 | 68.1 | 73.7 | 76.5 | 56.4 |
| selectivity for furfural [%] | 36.4 | 72 | 77.5 | 80.1 | 68.68 |

TABLE 4

| Sample no. | 19 | 20 | 21 | 22 | 23 | 24 |
|---|---|---|---|---|---|---|
| Target temperature [° C.] | 180 | 180 | 160 | 160 | 160 | 160 |
| holding time at target temperature [min] | 5 | 5 | 5 | 5 | 5 | 5 |
| Xylose feed in % | 4.8 | 4.9 | 5 | 5 | 5 | 5 |
| Kind of acid | MSA | H2SO4 | MSA | H2SO4 | MSA | H2SO4 |
| acid concentration in wt.-% | 2 | 2 | 4 | 4 | 6 | 6 |
| Weight of superimposed Me—THF [mg] | 10008 | 10010 | 10013 | 10023 | 10037 | 10016 |
| Amount of added NaCl [mg] | 254.8 | 253.7 | 252.6 | 254 | 256 | 250.4 |
| Amount of added Na-methansulfonate [mg] | 251 | 252.4 | 258.7 | 250.5 | 257.6 | 255.1 |
| Degree of conversation of xylose [%] | 97.3 | 99.4 | 66.5 | 73.8 | 88 | 84.4 |
| furfural yield [%] | 79.8 | 83 | 59.8 | 52.7 | 62.3 | 63.9 |
| selectivity for furfural [%] | 82 | 83.5 | 90 | 71.4 | 70.8 | 75.8 |

TABLE 5

| Sample no. | 25 | 26 |
|---|---|---|
| Target temperature [° C.] | 180 | 180 |
| holding time at target temperature [min] | 5 | 5 |
| Xylose feed in % | 4.8 | 4.9 |
| Kind of acid | MSA | MSA |
| acid concentration in wt.-% | 2 | 2 |
| Weight of superimposed Me—THF [mg] | 7030 | 4002 |
| Amount of added NaCl [mg] | 263.1 | 254.9 |
| Amount of added Na-methansulfonate [mg] | 250.4 | 251.5 |
| Degree of conversation of xylose [%] | 94.7 | 93.8 |
| furfural yield [%] | 75.2 | 70.1 |
| selectivity for furfural [%] | 79.3 | 74.7 |

TABLE 6

| Sample no. | 27 | |
|---|---|---|
| Target temperature [° C.] | 180 | in each thermal treatment |
| holding time at target temperature [min] | 5 | in each thermal treatment |
| Xylose feed in % | 4.82 | Newly added before each thermal treatment |
| Kind of acid | MSA | |
| acid concentration in wt.-% | 2 | |
| Weight of superimposed Me—THF [mg] | 10000 | Newly added before each thermal treatment |
| Concentration of NaCl [mg] | 258 | |
| Amount of added Na-methansulfonate [mg] | 251 | |
| Degree of conversation of xylose [%] | 98.53 | |
| furfural yield [%] | 76.42 | |
| selectivity for furfural [%] | 77.56 | |

In a first series of tests (table 1, samples 1-7), furfural production from aqueous feed mixtures comprising either methanesulfonic acid or sulfuric acid was studied. No salt was added to the feed mixture. Without significant influence of the kind of acid, at a target temperature of 160° C. and a holding time of 5 minutes (samples 1 and 2) the yield with regard to furfural is quite low. Increase of the holding time from 5 to 10 minutes results in some improvement (samples 3 and 4). Increase of the target temperature to 170° C. (samples 5 and 6) results in a more significant improvement (compared to samples 1 and 2) of yield and selectivity with regard to furfural when methanesulfonic acid is used instead of sulfuric acid. It is assumed that the lower improvement in the case of sulfuric acid is due to the formation of side products by sulfonation and coking.

In a second series of tests (table 2, samples 8-13), furfural production from aqueous feed mixtures comprising sodium chloride and either methanesulfonic acid or sulfuric acid was studied. In each test, the yield and selectivity with regard to furfural was increased, compared to the corresponding test under identical conditions (with the exception of the absence of sodium chloride) in table 1. With the exception of the tests at a holding temperature of 170° (samples 12 and 13) yield and selectivity with regard to furfural are higher when methanesulfonic acid is used instead of sulfuric acid. Accordingly, when methane sulfonic acid is used in combination with sodium chloride, the reaction may be performed at a lower temperature with higher yield and selectivity.

In a third series of tests (table 3, samples 14-18), furfural production from aqueous feed mixtures comprising methanesulfonic acid and one or more salts selected from the group consisting of sodium chloride, sodium methanesulfonate and sodium iodide was studied. The best results were obtained when a combination of either sodium chloride and sodium iodide or of sodium chloride and sodium methanesulfonate in a weight ratio around 1:1 is used. However, sodium iodide is less preferable because there is a risk of undesired oxidation of iodide to iodine.

In a fourth series of tests (table 4, samples 19-24), furfural production from aqueous feed mixtures comprising the preferred salt combination identified in the third series of tests (sodium chloride and sodium methanesulfonate in a weight ratio around 1:1) in combination with either methanesulfonic acid or sulfuric acid is studied, wherein the concentration of acid and the target temperature was varied. At a target temperature of 180° C. and an acid concentration of 2 wt.-% (samples 19 and 20), the results are similar, independent from the kind of acid used. Reduction of the target temperature to 160° C. with simultaneous increase of the acid concentration results in significant decrease of the degree of conversation of xylose and of the furfural yield (samples 21 and 22). However, with methanesulfonic acid better yield and selectivity with regard to furfural are obtained than with sulfuric acid. Further increase of the acid concentration at 160° C. results in an increase of the degree of conversation of xylose and the furfural yield (samples 23 and 24). But the selectivity with regard to furfural decreases with methanesulfonic acid (sample 23) Thus, with an aqueous feed solution comprising sodium chloride and sodium methanesulfonate in a weight ratio around 1:1, increase of the temperature has a more positive effect than increase of the acid concentration and addition of one or more salts (iii).

In a fifth series of tests (table 5, samples 25 and 26), furfural production from aqueous feed mixtures comprising the preferred salt combination identified in the third series of tests (sodium chloride and sodium methanesulfonate in a weight ratio around 1:1) in combination with methanesulfonic acid with reduced amount of extraction liquid is studied. The yield and selectivity with regard to furfural are somewhat lower than in sample 19 (see table 4) which was processed under identical conditions with the exception of the amount of extraction liquid. A lower amount of extraction liquid results in less efficient removal of the formed furfural from the aqueous feed mixture. However, the influence of reducing the amount of extraction liquid is not as significant as the influence of other parameters like temperature and acid concentration.

In a sixth series of tests (table 6, sample 27), it was studied whether from the aqueous liquid phase an aqueous mixture comprising methane sulfonic acid, sodium chloride and sodium methanesulfonate may be recovered and used for replenishing the aqueous feed mixture. For this test, an aqueous feed mixture was prepared and treated according to the parameters given in table 6. After completion of the thermal treatment and cooling, the phase of the extraction liquid was separated from the aqueous phase and stored. Xylose was added to the aqueous phase, fresh methyltetrahydrofurane was superimposed and a second thermal treatment was carried out under identical conditions like the preceding thermal treatment. Again, after completion of the thermal treatment and cooling, the phase of the extraction liquid was separated from the aqueous phase and stored. Xylose was added to the aqueous phase, fresh methyltetrahydrofurane was superimposed and a third thermal treatment was carried out under identical conditions like the preceding thermal treatments. After completion of the third thermal treatment and cooling, the phase of the extraction liquid was separated from the aqueous phase. The respective weight of the aqueous phase after the third thermal treatment and of the combined extraction liquid phases was determined and the respective concentrations of xylose and furfural in the aqueous phase after the third thermal treatment and in the combined extraction liquid phases were analyzed by means of HPLC. The results show that after completion of the thermal treatment from the aqueous phase an aqueous mixture comprising methane sulfonic acid, sodium chloride and sodium methanesulfonate may be recovered and used for replenishing the aqueous feed mixture without compromising the yield and selectivity with regard to furfural.

In an additional experiment, a xylose-containing biomass hydrolysate arising from acidic pretreatment of xylose-containing lignocellulose material was used as the educt. Using said freeze-dried solid residue as educt, an acidic aqueous solution was prepared by dissolving an amount of 250 mg of solid residue in 5 g of an aqueous solution of 2 wt.-% methanesulfonic acid. 5.25 g of this acidic aqueous solution of the solid residue were transferred in a reaction vessel, and 250 mg of sodium chloride and 250 mg of sodium methanesulfonate were added so as to obtain an aqueous feed mixture. The xylose-content in the dry residue was 43.5 wt.-% (as determined by HPLC).

After the added salt(s) were dissolved, the aqueous feed mixture in the reaction vessel was superimposed by an amount of 10 g of methyl-tetrahydrofurane (Me-THF) as the extraction liquid.

The reaction vessel was placed in a microwave apparatus and the sample was subjected to a thermal treatment by heating to a target temperatures of 180° C. and holding the sample at the target temperature at a pressure of 1600 kPa for a duration of five minutes The time to reach the target temperature was 48 seconds, starting from 20° C.

After completion of the thermal treatment at the target temperature the sample was cooled by means of a pressurized air jet. The aqueous phase and the phase of the extraction liquid were separated, and their respective weight was determined and the respective concentrations of xylose and furfural were analyzed by means of HPLC.

The furfural yield with respect to the solid residue used was 34%, whereas the yield based on the real xylose content of the solid residue was 78% which is similar to the result obtained under comparable conditions with crystalline xylose as the educt. Accordingly, the method of the invention is suitable for using as the starting material an aqueous mixture comprising one or more substances selected from the group consisting of xylose, oligosaccharides comprising xylose units and polysaccharides comprising xylose units directly obtained by processing cellulose-containing biomass, preferably lignocellulose, without further purification.

The invention claimed is:

1. Method for producing furfural comprising
providing an aqueous feed mixture comprising:
(i) one or more substances selected from the group consisting of xylose, oligosaccharides comprising xylose units, and polysaccharides comprising xylose units
(ii) methanesulfonic acid
(iii) one or more salts wherein the total concentration of (iii) said one or more salts is in the range of from 0.5 wt.-% to 20 wt.-% based on the total weight of said aqueous feed mixture,
contacting said aqueous feed mixture with an extraction liquid comprising one or more organic solvents, wherein said one or more solvents
have a higher solubility for furfural than said aqueous feed mixture and
are selected so that when said aqueous feed mixture is contacted with said extraction liquid two separate liquid phases are formed, wherein in a first liquid phase the concentration of water is higher than the concentration of said organic solvents and in a second liquid phase the concentration of said organic solvents is higher than the concentration of water
subjecting said aqueous feed mixture while contacted with said extraction liquid to a thermal treatment so that said one or more substances selected from the group consisting of xylose, oligosaccharides comprising xylose units, and polysaccharides comprising xylose units are reacted to furfural which is extracted from said aqueous feed mixture into said extraction liquid.

2. Method according to claim 1, wherein
the step of thermal treatment is conducted in a manner so that 80% by weight or more of said one or more salts (iii) provided in the aqueous feed mixture can be recovered.

3. Method according to claim 1, wherein
(iii) said one or more salts are selected from the group consisting of salts comprising a cation selected from the group consisting of cations of metals of groups I and II, and an anion selected from the group consisting of chloride, bromide, iodide, methanesulfonate, toluensulfonate, phosphate, tetrafluoroborate, trifluormethansulfonate, acetate, and nitrate.

4. Method according to claim 1, wherein
the aqueous feed mixture comprises two or more salts (iii).

5. Method according to claim 1, wherein in said aqueous feed mixture
the total concentration of (i) said one or more substances selected from the group consisting of xylose, oligosaccharides comprising xylose units, and polysaccharides comprising xylose units is in the range of from 1 wt.-% to 70 wt.-%,
wherein the concentration is based on the total weight of said aqueous feed mixture.

6. Method according to claim 1, wherein
said one or more organic solvents in said extraction liquid are selected from the group consisting of solvents having a boiling point which is below the boiling point of furfural
wherein in each case the boiling point is the boiling point at a pressure of 1000 hPa.

7. Method according to claim 1, wherein in said extraction liquid said one or more solvents are selected from the group consisting of tetrahydrofurane, methyl tetrahydrofurane, and dimethyl tetrahydrofurane.

8. Method according to claim 1, wherein in the step of contacting said aqueous feed mixture with said extraction liquid the weight ratio of said aqueous feed mixture to said extraction liquid is in the range of from 95:5 to 5:95.

9. Method according to claim 1, wherein the thermal treatment of the aqueous feed mixture in contact with the extraction liquid is carried out
at a temperature in the range of from 80° C. to 250° C.,
at a pressure in the range of from 100 kPa to 3000 kPa,
for a duration of from 1 seconds to 6 hours,
wherein the pressure and the temperature are selected so that said coexisting first and second liquid phases are maintained.

10. Method according to claim 1, further comprising
processing cellulose-containing biomass so that said one or more substances selected from the group consisting of xylose, oligosaccharides comprising xylose units, and polysaccharides comprising xylose units are formed, and
preparing said aqueous feed mixture comprising:
(i) said formed one or more substances selected from the group consisting of xylose, oligosaccharides comprising xylose units, and polysaccharides comprising xylose units,
(ii) methanesulfonic acid, and
(iii) one or more salts, wherein the total concentration of (iii) said one or more salts is in the range of from 0.5 wt.-% to 20 wt.-% based on the total weight of said aqueous feed mixture.

11. Method according to claim 10, wherein in said step of processing cellulose-containing biomass, a treatment mixture comprising cellulose-containing biomass, water, and methanesulfonic acid is subjected to a temperature in the range of from 100° C. to 210° C., at a pressure in the range of from 100 to 3000 kPa, wherein the pressure is selected so that at least a part of the water is in the liquid state.

12. Method according to claim 1, further comprising after completion of the thermal treatment one or both of the steps of
recovering from the first liquid phase an aqueous mixture comprising methane sulfonic acid (ii) and said one or more salts (iii), and using said recovered aqueous mixture for replenishing said aqueous feed mixture and/or
recovering from said second liquid phase said one or more organic solvents, and using said recovered one or more organic solvents for replenishing said extraction liquid.

13. Method according to claim 1, wherein
the aqueous feed mixture comprises
(i) said one or more substances selected from the group consisting of xylose, oligosaccharides comprising xylose units, and polysaccharides comprising xylose units in a total concentration of from 1 to 70 wt.-%,
(ii) methanesulfonic acid in a concentration of from 0.1 to 5 wt.-%,
(iii) both salts selected from the group consisting of sodium chloride and sodium methanesulfonate,
wherein the total concentration of sodium chloride and sodium methanesulfonate is in a range of from 0.5 to 20 wt.-%, and the weight ratio of sodium chloride to sodium methanesulfonate is in the range of from 10:1 to 1:10,
wherein the concentration in each case is based on the total weight of the aqueous feed mixture;
the extraction liquid comprises methyl tetrahydrofurane;
in the step of contacting said aqueous feed mixture and said extraction liquid the weight ratio of said aqueous feed mixture to said extraction liquid is in the range of from 95:5 to 5:95,
the thermal treatment the aqueous feed mixture in contact with the extraction liquid is carried out at a temperature in the range of from 130° C. to 220° C., for a duration of from 1 to 10 minutes at a pressure in the range of from 1200 kPa to 2000 kPa,
wherein the pressure and the temperature are selected so that said coexisting first and second liquid phases are maintained.

14. Method according to claim 4, wherein said two or more salts comprises
one salt selected from the group consisting of alkali metal chlorides and
one salt selected from the group of alkali metal salts of methanesulfonic acid.

15. Method according to claim 5, wherein in said aqueous feed mixture
the total concentration of (i) said one or more substances selected from the group consisting of xylose, oligosaccharides comprising xylose units, and polysaccharides comprising xylose units is in the range of from 10 wt.-% to 40 wt.-%,
wherein the concentration is based on the total weight of said aqueous feed mixture.

16. Method according to claim 8, wherein in the step of contacting said aqueous feed mixture with said extraction liquid the weight ratio of said aqueous feed mixture to said extraction liquid is in the range of from 60:40 to 50:50.

17. Method according to claim 1, wherein in said aqueous feed mixture
the concentration of (ii) methanesulfonic acid is in the range of 0.1 wt.-% to 5 wt.-%, based on the total weight of said aqueous feed mixture.

18. Method according to claim 1, wherein in said aqueous feed mixture
the total concentration of (iii) said one or more salts is in the range of from 5 wt.-% to 15 wt.-%, based on the total weight of said aqueous feed mixture.

19. Method according to claim 5, wherein in said aqueous feed mixture
the concentration of (ii) methanesulfonic acid is in the range of 1 wt.-% to 3 wt.-%, based on the total weight of said aqueous feed mixture.

20. Method according to claim 5, wherein in said aqueous feed mixture
the total concentration of (iii) said one or more salts is in the range of from 5 wt.-% to 15 wt.-%, based on the total weight of said aqueous feed mixture.

21. Method according to claim 9 wherein the thermal treatment is carried out at a temperature of 150° C. to 180° C. at a pressure of 1000 to 2500 kPa for a duration of 100 second to 30 minutes, wherein the pressure and temperature are selected so that said coexisting first and second liquid phases are maintained.

22. Method according to claim 13 wherein the thermal treatment is carried out at a temperature of 150° C. to 180° C.

* * * * *